(12) United States Patent
Wirtz et al.

(10) Patent No.: US 12,228,635 B2
(45) Date of Patent: Feb. 18, 2025

(54) MOTION TRACKING IN MAGNETIC RESONANCE IMAGING USING RADAR AND A MOTION DETECTION SYSTEM

(71) Applicant: KONINKLIJKE PHILIPS N.V., Eindhoven (NL)

(72) Inventors: Daniel Wirtz, Hamburg (DE); Tim Nielsen, Hamburg (DE); Christoph Leussler, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 1171 days.

(21) Appl. No.: 17/045,163

(22) PCT Filed: Mar. 29, 2019

(86) PCT No.: PCT/EP2019/057988
§ 371 (c)(1),
(2) Date: Oct. 3, 2020

(87) PCT Pub. No.: WO2019/192929
PCT Pub. Date: Oct. 10, 2019

(65) Prior Publication Data
US 2021/0146158 A1    May 20, 2021

(30) Foreign Application Priority Data
Apr. 5, 2018    (EP) .................................... 18165812

(51) Int. Cl.
*G01S 13/86* (2006.01)
*A61N 5/10* (2006.01)
(Continued)

(52) U.S. Cl.
CPC ............ *G01S 13/86* (2013.01); *A61N 5/1049* (2013.01); *G01R 33/283* (2013.01);
(Continued)

(58) Field of Classification Search
CPC ........ G01S 13/86; G01S 13/88; G01S 17/894; A61N 5/1049; A61N 2005/1055; G01R 33/283; G01R 33/4814; G01R 33/5673
See application file for complete search history.

(56) References Cited

U.S. PATENT DOCUMENTS 6,417,797 B1    7/2002    Cousins et al.
9,764,162 B1 *  9/2017    Willcut ................. G06T 7/0014
(Continued)

FOREIGN PATENT DOCUMENTS

| | | |
|---|---|---|
| CN | 104605889 A | 5/2015 |
| DE | 102008019862 A1 | 10/2009 |
| WO | 2007063516 A2 | 6/2007 |

OTHER PUBLICATIONS

Verkrysse et. al, "Remote plethysmographic imaging using ambient light" Optics Express 16(26)21434, 2008.
(Continued)

*Primary Examiner* — Sean A Frith

(57) ABSTRACT

The invention provides for a medical instrument (100, 300, 400, 500) comprising a magnetic resonance imaging system (102). The medical instrument further comprises a subject support (120) with a support surface (121) configured for supporting at least a portion of the subject within an imaging zone (108). The subject support comprises a radar array (125) embedded below the support surface. The medical instrument further comprises a radar system (124) for acquiring a radar signal (144) from the subject. The medical instrument further comprises a motion detection system (122) configured for acquiring a movement signal (146). Execution of machine executable instructions (140) causes a processor (130) to: continuously (200) receive the radar signal; continuously (202) receive the movement signal; continuously (204) calculate a combined motion signal (148) from the radar system and the movement signal; and (Continued)

control (206) the magnetic resonance imaging system with the pulse sequence commands to acquire the magnetic resonance imaging data, wherein the acquisition of the magnetic resonance imaging data is controlled using the combined motion signal.

20 Claims, 10 Drawing Sheets

(51) Int. Cl.
   *G01R 33/28* (2006.01)
   *G01R 33/48* (2006.01)
   *G01R 33/567* (2006.01)
   *G01S 13/88* (2006.01)
   *G01S 17/894* (2020.01)

(52) U.S. Cl.
   CPC ..... *G01R 33/4814* (2013.01); *G01R 33/5673* (2013.01); *G01S 13/88* (2013.01); *A61N 2005/1055* (2013.01); *G01S 17/894* (2020.01)

(56) References Cited

U.S. PATENT DOCUMENTS

| | | | | |
|---|---|---|---|---|
| 2002/0065461 | A1* | 5/2002 | Cosman | G06T 7/73 |
| | | | | 600/429 |
| 2005/0128123 | A1 | 6/2005 | Greneker et al. | |
| 2009/0088623 | A1* | 4/2009 | Vortman | A61B 8/5276 |
| | | | | 601/3 |
| 2009/0192384 | A1* | 7/2009 | Fontius | A61B 6/527 |
| | | | | 600/425 |
| 2010/0060276 | A1* | 3/2010 | Zur | G01R 33/56333 |
| | | | | 324/309 |
| 2010/0271615 | A1 | 10/2010 | Sebastian et al. | |
| 2011/0066027 | A1 | 3/2011 | Schnell | |
| 2012/0330151 | A1 | 12/2012 | Weinstein et al. | |
| 2013/0093866 | A1* | 4/2013 | Ohlhues | G02B 23/2476 |
| | | | | 348/65 |
| 2013/0165770 | A1 | 6/2013 | Li et al. | |
| 2014/0073908 | A1* | 3/2014 | Biber | G01R 33/56308 |
| | | | | 324/322 |
| 2014/0194728 | A1 | 7/2014 | Vahala | |
| 2014/0194793 | A1* | 7/2014 | Nakata | G01S 13/825 |
| | | | | 601/48 |
| 2014/0275966 | A1* | 9/2014 | Schwartz | A61B 8/085 |
| | | | | 600/437 |
| 2015/0293201 | A1 | 10/2015 | Assmann et al. | |
| 2015/0320342 | A1 | 11/2015 | Biber et al. | |
| 2015/0366527 | A1* | 12/2015 | Yu | G06T 7/0012 |
| | | | | 600/407 |
| 2016/0270691 | A1 | 9/2016 | Yu et al. | |
| 2017/0065832 | A1* | 3/2017 | Berlinger | G16H 50/50 |
| 2017/0319143 | A1* | 11/2017 | Yu | A61B 5/682 |
| 2018/0059202 | A1* | 3/2018 | Bito | G01R 33/4625 |
| 2018/0193674 | A1* | 7/2018 | Brooks | A61N 5/1084 |

OTHER PUBLICATIONS

Scully et. al., "Physiological parameter monitoring from optical recordings with a mobile phone" IEEE Trans Biomed Eng. 2012;59:303-306.

Paulson et. al., "Ultra-wideband Radar Methods and Techniques of Medical Sensing and Imaging" SPIE Intl. Symp. On Optics East, Boston Oct. 23-26, 2005.

Frauenrath T, Hezel F, Renz W, de Geyer d'Orth T, Dieringer M, von Knobelsdorff-Brenkenhoff F, Prothmann M, Schulz-Menger J, Niendorf T. "Acoustic cardiac triggering: a practical solution for synchronization and gating of cardiovascular magnetic resonance at 7 Tesla" J Cardiovasc Magn Reson 2010;12:67.

Feinberg DA, Giese D, Bongers DA, Ramanna S, Zaitsev M, Markl M, Gunther M. "Hybrid ultrasound MRI for improved cardiac imaging and real-time respiration control" Magn Reson Med 2010;63:290-296.

Kording, F., Schoennagel, B., Lund, G., Ueberle, F., Jung, C., Adam, G. and Yamamura, J. (2015), "Doppler ultrasound compared with electrocardiogram and pulse oximetry cardiac triggering: A pilot study" Magn. Reson. Med., 74: 1257-1265. doi:10.1002/mrm. 25502.

Thiel et al "Combining Magnetic Resonance Imaging and Ultrawideband Radar: A New Concept for Multimodal Biomedical Imaging" Review of Scientific Instruments 80 (2009).

International Search Report and Written Opinion from PCT/EP2019/057988 mailed Jul. 3, 2019.

Ali et al "Ultra-Wideband Antenna Development to Enhance Gain for Surface Penetrating Radar" Wireless Personal Communications Springer Nature 2020.

* cited by examiner

MOTION TRACKING IN MAGNETIC RESONANCE IMAGING USING RADAR AND A MOTION DETECTION SYSTEM

CROSS REFERENCE TO RELATED APPLICATIONS

This application is a U.S. national phase application of International Application No. PCT/EP2019/057988 filed on Mar. 29, 2019, which claims the benefit of EP application Ser. No. 18165812.1 filed on Apr. 5, 2018 and is incorporated herein by reference.

FIELD OF THE INVENTION

The invention relates to magnetic resonance imaging, in particular to the control of magnetic resonance imaging using RADAR.

BACKGROUND OF THE INVENTION

A large static magnetic field is used by Magnetic Resonance Imaging (MRI) scanners to align the nuclear spins of atoms as part of the procedure for producing images within the body of a patient. Various quantities or properties of the subject can be measured spatially using MRI. However, the acquisition of magnetic resonance imaging data is not instantaneous. The subject can move during the acquisition of data spoiling the acquisition. There exist various methods for compensating for the motion of a subject which include the gating of the data acquisition.

United States patent publication US 2005/0128123 A1 discloses a system and method for suppressing motion artifacts introduced by movement of a radar detection system. Briefly described, in architecture, one embodiment of the system, among others, can be implemented as follows. The system includes a Doppler radar module configured to transmit a microwave signal directed towards an object and receive the reflected microwave signals from the object and a living subject positioned behind the object. Also, the system includes a reference module configured to transmit a reference signal towards the object and receive the reflected reference signal from the object. By comparing the two reflected signals from the Doppler radar module and the reference device, a signal processor suppresses motion artifacts generated by movement of the Doppler radar module to identify the presence of the living subject behind the object. Other systems and methods are also provided.

United States patent application publication US 2010/0271615 A1 discloses a system that uses range and Doppler velocity measurements from a lidar system and images from a video system to estimate a six degree-of-freedom trajectory of a target. The system estimates this trajectory in two stages: a first stage in which the range and Doppler measurements from the lidar system along with various feature measurements obtained from the images from the video system are used to estimate first stage motion aspects of the target (i.e., the trajectory of the target); and a second stage in which the images from the video system and the first stage motion aspects of the target are used to estimate second stage motion aspects of the target. Once the second stage motion aspects of the target are estimated, a three-dimensional image of the target may be generated.

The US patent application US2014/0073908 discloses an MRI-system with a motion sensor unit for detecting movement of the patient. The known motion sensor unit may be integrated in the RF receiver coil.

SUMMARY OF THE INVENTION

The invention provides for a medical instrument, a computer program product, and a method in the independent claims. Embodiments are given in the dependent claims.

Radar systems such as ultra-wide band radar have been used for measuring the motion of subject for magnetic resonance imaging. However, the radar signal used to guide or trigger the magnetic resonance imaging may be corrupted or contain noise. Embodiments may improve this by using an additional motion detection system to simultaneously measure a movement signal which may be combined and/or correlated with the radar signal. For example, data from a camera and/or an ultrasound imaging system (such as a doppler ultrasonic imaging system) may be used. This may result in a more robust combined motion signal which can be used for such things as triggering and controlling the acquisition of magnetic resonance imaging data or even the control of a radiotherapy device.

In one aspect the invention provides for a medical instrument comprising a magnetic resonance imaging system that is configured for acquiring magnetic resonance imaging data from an imaging zone. The magnetic resonance imaging system comprises a subject support configured for supporting at least a portion of the subject within the imaging zone. The subject support comprises a support surface for receiving the subject. The subject support comprises a, radar array, in particular embedded below the support surface. In some examples the radar array may be embedded within the subject support. In other embodiments the support surface is formed by an overlay or attachment which comprises a radar array which is placed on the subject support.

The magnetic resonance imaging system further comprises a radar system for acquiring a radar signal from the subject. The radar system comprises the radar array. The medical instrument further comprises a motion detection system configured for acquiring a movement signal from the subject. The motion detection system may take different forms in different examples. In one example the motion detection system is an optical or camera system that is used to measure motion or respiration of the subject. In other examples the motion detection system may for example be an ultrasound imaging system.

The medical instrument further comprises a memory for storing machine-executable instructions and pulse sequence commands. The pulse sequence commands are instructions or data which may converted into such instructions or commands which may be used for controlling the magnetic resonance imaging system to acquire magnetic resonance imaging data. The medical instrument further comprises a processor for controlling the medical instrument. Execution of the machine-executable instructions causes the processor to continuously receive the radar signal from the radar system. Execution of the machine-executable instructions further causes the processor to continuously receive the movement signal from the motion detection system.

Execution of the machine-executable instructions further causes the processor to continuously calculate a combined motion signal from the radar system and the movement signal. The radar signal and the movement signal may for example be digitally sampled. In this context references herein to continuously may be interpreted as repeatedly. For example, the radar signal and the movement signal may be sampled digitally and transferred to the processor at a particular data rate or in groups of data. When the radar signal and the movement signal are received by the processor the processor may respond by calculating the combined motion signal.

Execution of the machine-executable instructions further causes the processor to control the magnetic resonance imaging system with the pulse sequence commands to acquire the magnetic resonance imaging data. The acquisition of the magnetic resonance imaging data is controlled at least partially using the combined motion signal. For example, the combined motion signal may be used to gate the acquisition of the magnetic resonance imaging data so that images in respect to a particular movement phase such as cardiac or respiratory phase may be made. In other examples the movement or combined motion signal may be used to control how the magnetic resonance imaging data is acquired during operation with another portion of the medical instrument.

This embodiment may be beneficial because the combination of the radar signal and the movement signal may enable a more accurate motion signal to be calculated or it may enable a motion signal which is less susceptible to noise.

The combined motion signal may for example be used for gating the magnetic resonance acquisition of the heart and/or breathing signals. The combined motion signal may also be useful for gating a radio therapy system.

In another embodiment the radar system is an ultra-wideband or UWB radar system. In other examples the radar system may be a FMCW radar system. In other examples the radar system may be a narrowband/dual band radar system.

In another embodiment the combined motion signal comprises any one of the following: a cardiac phase motion signal, a breathing phase motion signal, a voluntary motion signal, and combinations thereof. The combined motion signal may be beneficial because the breathing of the subject may affect the measurement of the cardiac phase. The combination of two data types which are present in the movement signal and the radar signal may help to deconvolve the multiple types of motion. The voluntary motion signal may for example be descriptive of the gross motion or position of the subject. As a subject moves it may be difficult for a single modality to accurately measure something such as the cardiac phase or the breathing phase of a subject. By combining for example, a camera with the radar signal it may be possible to measure a cardiac phase motion signal and/or breathing phase motion while the subject is moving or changing his or her position.

In another embodiment the combined motion signal is calculated by cross correlating the radar signal with the movement signal to identify similar signals and reject false signals. This embodiment may be beneficial because it may increase the signal-to-noise ratio or reduce errors when calculating the combined motion signal.

In another embodiment the combined motion signal is calculated by multiplying the radar signal with the movement signal to determine when the radar signal and the movement signal coincide. This may be beneficial because both the radar signal and the movement signal each have an amplitude that could be used separately as a trigger. The multiplication of the radar signal and the movement signal provides a consistent means of combining the two signals. There may be a phase difference or delay between the two signals, but this effect will be consistent. In another embodiment the combined motion signal is calculated by adding the radar signal with the movement signal using a corrective phase shift. For example, the motion velocity can be obtained with the Doppler frequency shift of the radar signal. This may be useful in correcting the phase between the radar signal and the movement signal.

Correlation Between Optical System and RADAR System

In another embodiment the combined motion signal is continuously calculated using a machine learning algorithm. The machine learning algorithm may take different forms in different examples. For example, there may be a statistical learning method which may also be created with fitting a model to the acquired radar signal and movement signal. In other examples neural networks that use for example convolution neural networks and/or deep learning may be used to process the radar signal and the movement signal into the combined motion signal. The use of neural networks may be particularly beneficial because neural networks excel at identifying patterns. The particular patterns of the radar signal and the motion signals may therefore be combined using deep learning.

In another embodiment the machine-executable instructions further cause the processor to receive a preliminary radar signal from the radar system. Execution of the machine-executable instructions further cause the processor to receive a preliminary movement signal from the motion detection system. The preliminary movement signal is acquired simultaneously with the preliminary radar signal. Execution of the machine-executable instructions further cause the processor to receive a heart rate signal from a heart rate monitor. The heart rate signal is acquired simultaneously with the preliminary radar signal. Execution of the machine-executable instructions further cause the processor to receive a breathing signal from a breathing monitor. The breathing signal is acquired simultaneously with the preliminary radar signal.

Execution of the machine-executable instructions further cause the processor to train the machine learning algorithm using the preliminary radar signal, the preliminary movement signal, the heart rate signal, and the breathing signal. This embodiment may be performed for a large number of subjects before the examination or it may be performed before the particular subject which is being imaged by the magnetic resonance imaging system. In any case in this example the radar signals and movement signals are compared to independent data such as a heart rate signal and the breathing signal so that the machine learning algorithm can be trained directly. For example, the heart rate signal and the breathing signal may be used for output in training a neural network. The preliminary radar signals and the preliminary movement signals may for example be for a specific subject or it may be taken from groups of subjects which are used for the training process.

In another embodiment the machine learning algorithm in an unsupervised statistical learning algorithm. Execution of the machine-executable instructions further cause the processor to train the machine learning algorithm on the fly as the radar signal and movement signal are received. Statistical learning algorithms may involve fitting a model to a data. The statistical learning algorithm could for example be adapted to a particular subject during the acquisition of the radar signal and the movement signal for that subject.

In another embodiment the one or more movement signal and the radar signal supplies a cardiac motion signal. The other of the movement signal and the radar signal supplies a body motion signal. Execution of the machine-executable instructions further cause the processor to calculate a motion vector field using cardiac motion signal and the body motion signal. The cardiac phase motion signal is de-noised using the motion vector field. This embodiment may be beneficial because the gross motions of the subject's body as described by the body motion signal can be used to refine and improve the cardiac motion signal.

In another embodiment the motion signal comprises chest motion. The motion detection system comprises a camera for detecting the chest motion. This may be beneficial because the camera may be used to measure the breathing of the subject in a non-contact way.

Examples of cameras that can be used are for example an infrared camera, a color camera, a black and white camera, and a three-dimensional or 3D camera.

In another embodiment the camera can also optionally detect if there is a surface coil on the subject. When detecting chest motion the chest motion may be detected by measuring direct motion of the subject, by measuring the change in position of garments being worn by the subject, or even by a change in position of surface coils that have been placed onto the subject.

In another embodiment the magnetic resonance imaging system further comprises a remotely controllable camera mount configured for remotely pointing the camera. Execution of the machine-executable instructions further cause the processor to determine a focus location using the radar signal. Execution of the machine-executable instructions further cause the processor to control the remotely controllable camera mount to point the camera at the focus location. This embodiment may be beneficial because the radar system may be useful in detecting gross or broad motions of the subject. Using the radar system, the best location to aim the camera can be detected. The camera is then aimed at this focus location and then the motion data from the camera can be used to further refine the motion detected by the radar signal.

In another embodiment the motion detector system comprises an ultrasound imaging system. The use of an ultrasound imaging system may be beneficial because the data acquired by the ultrasound imaging system is complimentary to the data obtained by the radar system.

In another embodiment the ultrasound imaging system comprises an ultrasound transducer array distributed across the support surface. For example, ultrasound transducers may be placed about or in the middle of elements of the radar array.

In another embodiment the ultrasound imaging system is a HIFU system mounted in the subject support. This embodiment may be beneficial because the HIFU system may be useful for both acquiring the movement signal and also for performing sonications on locations in the subject. The combined motion signal may for example be useful for adjusting the targeting or gating the sonication of the subject using a HIFU system.

In another embodiment the ultrasound imaging system has an adjustable field of view. Execution of the machine-executable instructions further cause the processor to determine a focus location using the radar signal and to control the adjustable field of view so that the focus location is within the adjustable field of view. For example, if there is a number of ultrasonic transducers distributed across the support service the radar system can be used to first determine which transducers should be used to image the subject to measure the movement signal with the ultrasound imaging system. This may have the effect of increasing the likelihood that the combined motion signal has less noise and contains a more relevant signal for tracking the motions of the subject.

In another embodiment the medical instrument further comprises a radiotherapy system. Execution of the machine-executable instructions further cause the processor to receive radiotherapy instructions configured for controlling the radiotherapy system to irradiate a target zone of the subject. Execution of the machine-executable instructions further cause the processor to control the radiotherapy system to irradiate the target zone using the radiotherapy instructions and the combined motion signal. The combined motion signal is used to modify the radiotherapy instructions and/or gate irradiation by the radiotherapy system. This embodiment may be beneficial because the combined motion signal can be used to improve the targeting of the radiotherapy system.

In another embodiment the magnetic resonance imaging system is configured for performing a moving bed magnetic resonance imaging protocol. This is a protocol where the bed is moved into the magnetic resonance imaging system and magnetic resonance imaging is performed at the same time or in steps. During movement of the subject support both the radar signal and the movement signal may be detected and measured. The signals may both be filtered and correlated. At certain positions of the subject support one or the other of the signals may be sufficient. This may provide for the benefit of improving the tracking and motion during a moving bed magnetic resonance imaging protocol.

In another aspect the invention provides for a computer program product comprising machine-executable instructions configured for being executed by a processor controlling the medical instrument. The medical instrument comprises a magnetic resonance imaging system for acquiring magnetic resonance imaging data from an imaging zone. The medical instrument comprises a subject support configured for supporting at least a portion of the subject within the imaging zone. The subject support comprises a support service for receiving the subject. The subject support comprises a radar array embedded below the support surface. The medical instrument further comprises a radar system for acquiring radar signals from the subject. The radar system comprises the radar array.

The medical instrument further comprises a motion detection system configured for acquiring a movement signal from the subject. Execution of the machine-executable instructions further cause the processor to continuously receive the radar signal from the radar system. Execution of the machine-executable instructions further cause the processor to continuously receive the movement signal from the motion detection system. Execution of the machine-executable instructions further cause the processor to continuously calculate a combined motion signal from the radar system and the movement signal. Execution of the machine-executable instructions further cause the processor to control the magnetic resonance imaging system with pulse sequence commands to acquire the magnetic resonance imaging data. The acquisition of the magnetic resonance imaging data is controlled using the combined motion signal. The advantages of this embodiment have been previously discussed.

In another aspect the invention provides for a method of operating a medical instrument. The medical instrument comprises a magnetic resonance imaging system for acquiring magnetic resonance imaging data from an imaging zone. The medical instrument comprises a subject support configured for supporting at least a portion of the subject within the imaging zone. The subject support comprises a support surface for receiving the subject. The subject support comprises a radar array embedded below the support surface. The medical instrument further comprises a radar system for acquiring a radar signal from the subject. The radar system comprises the radar array.

The medical instrument further comprises a motion detection system configured for acquiring a movement signal from the subject. The method comprises continuously receiving the radar signal from the radar system. The method further comprises continuously receiving the movement signal from the motion detection system. The method further comprises continuously calculating a combined motion signal from the radar system and the movement signal. The method further comprises controlling the magnetic resonance imaging system with the pulse sequence commands to acquire the magnetic resonance imaging data. The acquisition of the magnetic resonance imaging data is controlled using the combined motion signals.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. Computer memory may be any volatile or non-volatile computer-readable storage medium.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the C programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include but are not limited to: a universal serial bus, IEEE 1394 port, parallel port, IEEE 1284 port, serial port, RS-232 port, IEEE-488 port, bluetooth connection, wireless local area network connection, TCP/IP connection, ethernet connection, control voltage interface, MIDI interface, analog input interface, and digital input interface.

Magnetic Resonance (MR) data is defined herein as being the recorded measurements of radio frequency signals emitted by atomic spins using the antenna of a magnetic resonance apparatus during a magnetic resonance imaging scan. Magnetic resonance data or magnetic resonance imaging data is an example of medical imaging data. A Magnetic Resonance (MR) image is defined herein as being the reconstructed two or three-dimensional visualization of anatomic data contained within the magnetic resonance imaging data.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
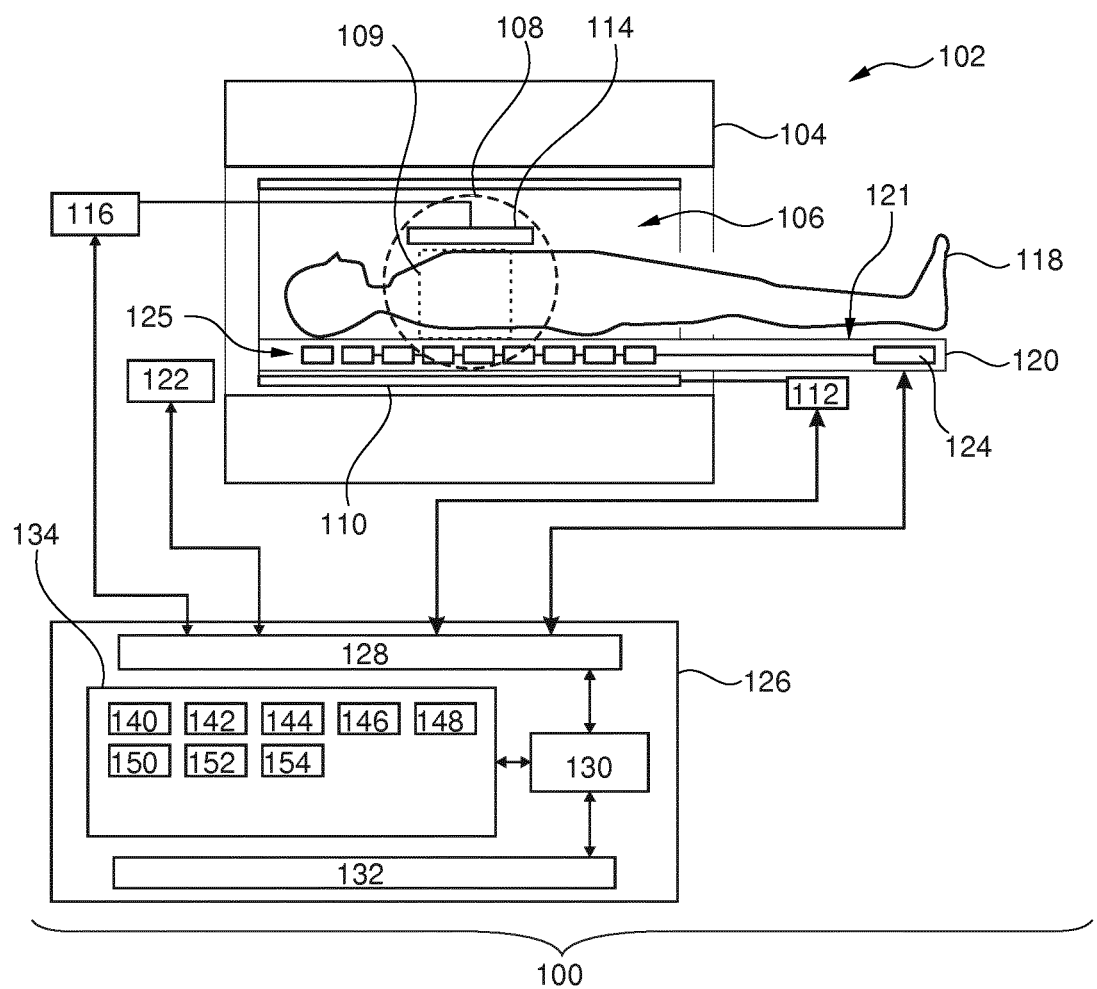
FIG. 1 illustrates an example of a medical instrument.

FIG. 1 shows an example of a medical instrument 100 that magnetic resonance imaging system 102 with a magnet 104. The magnet 104 is a superconducting cylindrical type magnet with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging. A region of interest 109 is shown within the imaging zone 108. The magnetic resonance imaging data that is acquired typically acquired for the region of interest. A subject 118 is shown as being supported by a subject support 120 such that at least a portion of the subject 118 is within the imaging zone 108 and the region of interest 109.

Within the bore 106 of the magnet there is also a set of magnetic field gradient coils 110 which is used for acquisition of preliminary magnetic resonance imaging data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receivers. The radio-frequency coil 114 may also have multiple receive/transmit elements and the radio frequency transceiver 116 may have multiple receive/transmit channels. For example if a parallel imaging technique such as SENSE is performed, the radio-frequency could 114 will have multiple coil elements.

A subject support 120 is shown as supporting a subject 118 in the imaging zone. The subject support 120 has a support surface 121 that is configured for receiving the subject 118. There is a radar system 124 that is shown as being positioned within the subject support 120. The radar system 124 also comprises a radar array 125 that is below the support surface 121 and pointed towards the subject 118. The multiple elements of the radar array 125 enable measurements of the motion of the subject 118 to be measured. This includes both internal and external motion of the subject 118. The box 122 is intended to represent a motion detection system 122. Further examples of the motion detection system 122 are detailed in further Figs.

The magnetic field gradient coil power supply 112, the transceiver 116, the motion detection system 122 and the radar system 124 are shown as being connected to the hardware interface 128 of the computer system 126. The computer system further comprises a processor 130 that is in communication with the hardware system 128, a memory 134, and a user interface 132. The memory 134 may be any combination of memory which is accessible to the processor 130. This may include such things as main memory, cached memory, and also non-volatile memory such as flash RAM, hard drives, or other storage devices. In some examples the memory 134 may be considered to be a non-transitory computer-readable medium.

The memory 134 is shown as containing machine-executable instructions 140. The machine-executable instructions 140 enable the processor 130 to control the operation and function of the magnetic resonance imaging system 100. The machine-executable instructions 140 may also enable the processor 130 to perform various data analysis and calculation functions. The computer memory 134 is further shown as containing pulse sequence commands 142. The pulse sequence commands are configured for controlling the magnetic resonance imaging system 100 to acquire a series of magnetic resonance imaging data from the subject 118 according to a magnetic resonance imaging protocol.

The memory 134 is further shown as containing a radar signal 144 that was acquired with the radar system 124. The memory 134 is further shown as containing a movement signal 146 that was recorded by the motion detection system 122. The memory 134 is further shown as comprising a combined motion signal 148 that was calculated using the radar system 144 and the movement signal 146. The combined motion signal 148 may for example take different forms in different examples. It may be a cardiac signal, a breathing phase signal, or even a combination of the two. The combined motion signal 148 may also contain details about the gross or large movements of the subject 118.

The memory 134 is further shown as containing magnetic resonance imaging data 150 that was acquired by controlling the magnetic resonance imaging system 102 with the pulse sequence commands 142. The memory 134 is further shown as containing a magnetic resonance image 152 that was reconstructed from the magnetic resonance imaging data 150. The magnetic resonance imaging data 150 may be partially controlled using the combined motion signal 148. For example, the combined motion signal 148 may be used for gating or otherwise adjusting the control of the magnetic resonance imaging data.

The memory 134 is further shown as containing an optional machine learning algorithm 154 that may be used for calculating the combined motion signal 148 from the radar system 144 and the movement signal 146.

Figure 2:
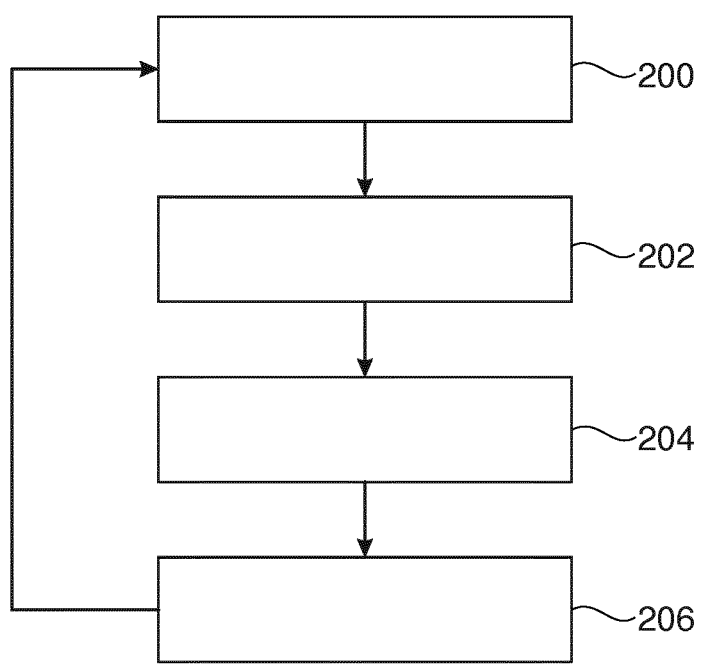
FIG. 2 shows a flow chart which illustrates a method of operating the medical instrument of FIG. 1.

FIG. 2 shows a flowchart which illustrates a method of operating the medical instrument 100 of FIG. 1. The method illustrated in FIG. 2 functions as a control loop. First in step 200 the radar signal 144 is received. Next in step 202 the movement signal 146 is received. Steps 200 and 202 may be performed simultaneously or in either order. The receiving of the radar system 144 and the movement signal 146 may for example be in the form of digital data. In this case the radar signal 144 and the movement signal 146 may be acquired in discreet chunks of data. Although they are acquired discreetly they may be acquired in a regular or repetitious fashion in which case they constitute the continuous acquisition of data. Next in step 204 the combined motion signal 148 is calculated from the radar signal 144 and the movement signal 146. Next in step 206 the magnetic resonance imaging system 102 is controlled with the pulse sequence commands 142 to acquire the magnetic resonance imaging data 150. The combined motion signal 148 may for example be used to gate the acquisition of the magnetic resonance imaging data 150 or to adjust the pulse sequence commands 142 during the acquisition.

Figure 3:
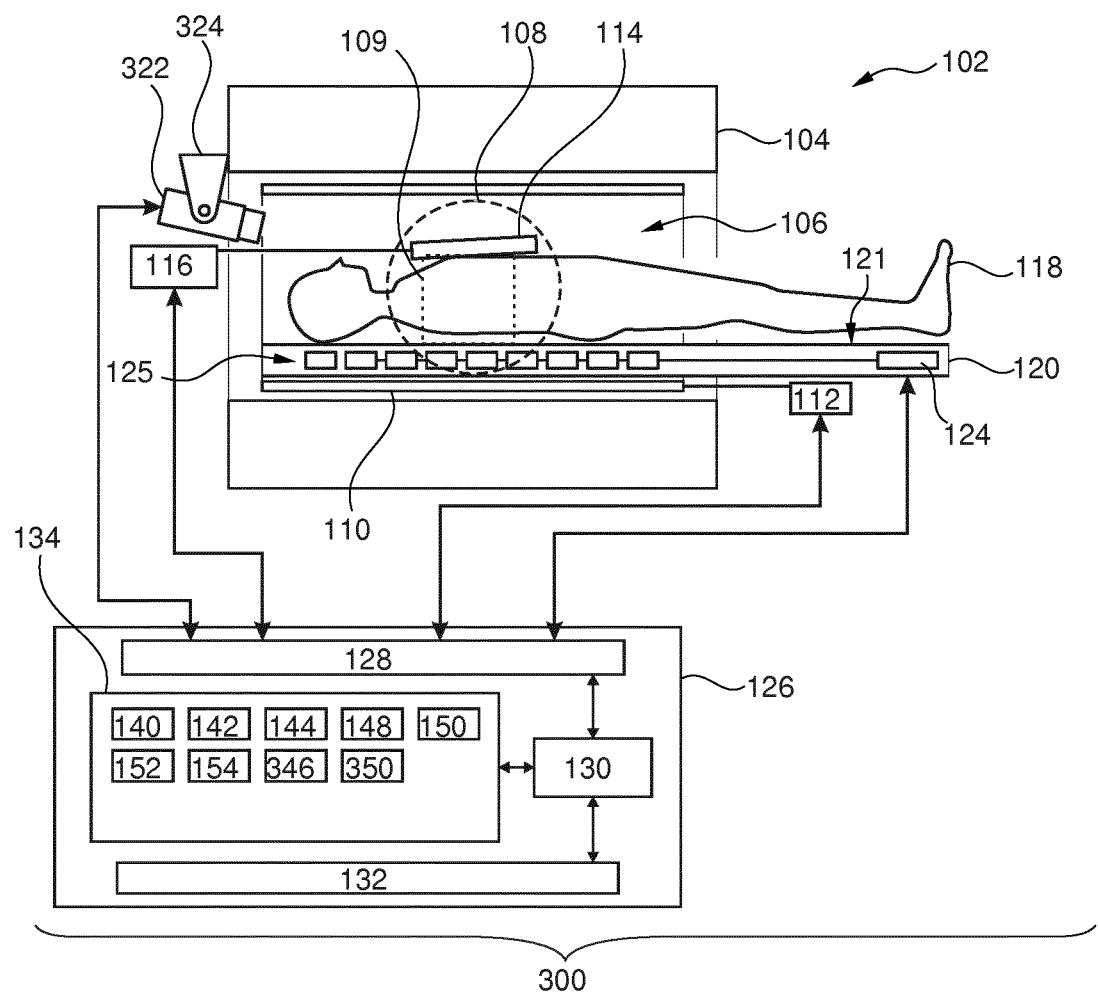
FIG. 3 illustrates a further example of a medical instrument.

FIG. 3 shows a further example of a medical instrument 300. The example illustrated in FIG. 3 is similar to that as is illustrated in FIG. 1. In FIG. 3 the motion detection system is a camera 322. The camera is shown as being attached to an optional remotely controllable camera mount 324. The remotely controllable camera mount 324 allows the focus location of the camera 322 to be remotely adjusted.

The memory 134 is shown as containing image data 346. The image data was recorded by the camera 322 and is an example of a movement signal. The radar system 124 may for example be useful in determining what portion of the subject 118 could be best measured using the camera 322. The memory 134 is shown as optionally containing a focus location 350 that was determined using the radar signal 144. The focus location 350 may then be used to generate commands which cause the remotely controllable camera mount 324 to adjust the location of the camera 322.

In this example the radio-frequency coil 114 is a surface coil which has been placed on the chest of the subject 118. The camera 322 could for example measure the image data 346 which is then converted into the movement signal 146 by noting a change in the position of the radio-frequency coil 114 as the subject 118 breathes. In other examples the camera 322 may look directly at the chest of the subject 118 or may track the motion of garments being worn by the subject 118.

Figure 4:
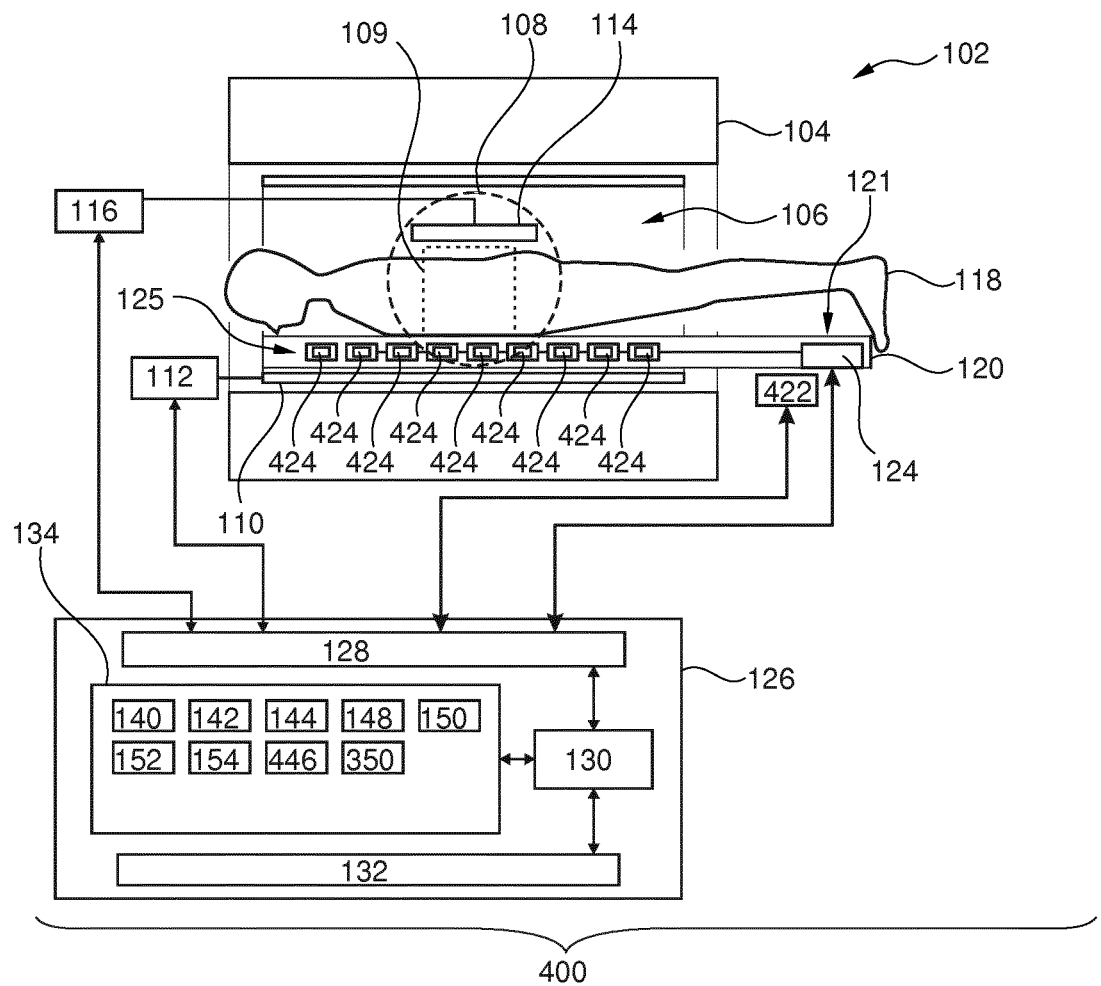
FIG. 4 illustrates a further example of a medical instrument.

FIG. 4 shows a further example of a medical instrument 400. The example illustrated in FIG. 4 is similar to that of the medical instrument in FIG. 1. In this example the motion detection system is an ultrasound imaging system 422. There are ultrasound transducers 424 which are interspersed within the subject support 120. Connections between the ultrasound imaging system 422 and the ultrasound transducers 424 are not shown. The memory 134 is shown as containing ultrasound data 446 that was acquired using the ultrasound imaging system 422, such as a doppler imaging ultrasound imaging system. The ultrasound data 446 is an example of the movement signal 146.

In order to determine which ultrasound transducers 424 should be used for measuring the ultrasound data the radar system 124 can be used to initially determine a focus location 350. The focus location 350 can be used to select which ultrasound transducers 424 to use to measure the ultrasound data 446.

Figure 5:
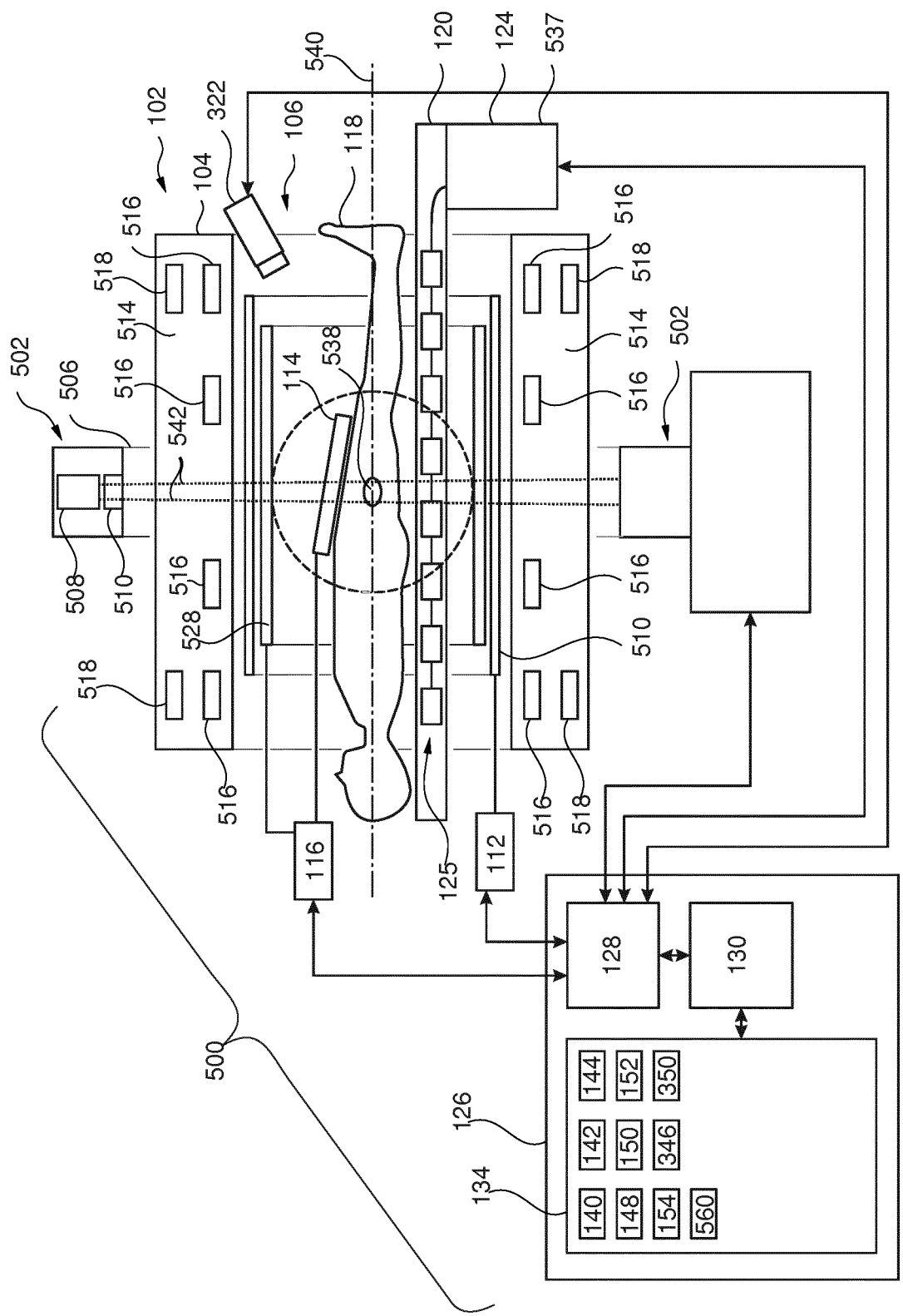
FIG. 5 illustrates a further example of a medical instrument.

FIG. 5 illustrates a further example of a medical instrument 500. The example illustrated in FIG. 5 is similar to the example illustrated in FIG. 3 except the medical instrument further comprises a radiotherapy system 502. In this particular example the radiotherapy system is a LINAC, however other radiotherapy systems could be substituted for the LINAC system.

The radiotherapy system 502 comprises a gantry 506 and a radiotherapy source 508. The gantry 506 is for rotating the radiotherapy source 508 about an axis of gantry rotation 540. Adjacent to the radiotherapy source 508 is a collimator 510.

The magnet 112 shown in this embodiment is a standard cylindrical superconducting magnet. The magnet 112 has a cryostat 514 with superconducting coils within it 516. There are also superconducting shield coils 518 within the cryostat also.

As in FIG. 1 there is a magnetic resonance coil 114 connected to a transceiver 116. Also shown in FIG. 5 is an optional body coil 528 attached to the transceiver.

The subject support 120 may be positioned by an optional mechanical positioning system 537. Within the subject 118 there is a target zone 538. The axis of gantry rotation 540 is coaxial in this particular embodiment with the cylindrical axis of the magnet 104. The subject support 120 has been positioned such that the target zone 538 lies on the axis 540 of gantry rotation. The radiation source 508 is shown as generating a radiation beam 542 which passes through the collimator 510 and through the target zone 538. As the radiation source 508 is rotated about the axis 540 the target zone 538 will be targeted by the radiation beam 542. The radiation beam 542 passes through the cryostat 514 of the magnet.

The mechanical positioning system 537 and the radiotherapy system 502 are shown as being additionally connected to the hardware interface 128 of the computer system 126.

The computer memory 134 is further shown as containing radiotherapy instructions 560. The radiotherapy instructions are instructions or commands which can be converted into such commands which can control the radiotherapy system 502 to irradiate the target zone 538. The execution of the radiotherapy instructions 560 may be modified or gated using the combined motion signal 148.

Figure 6:
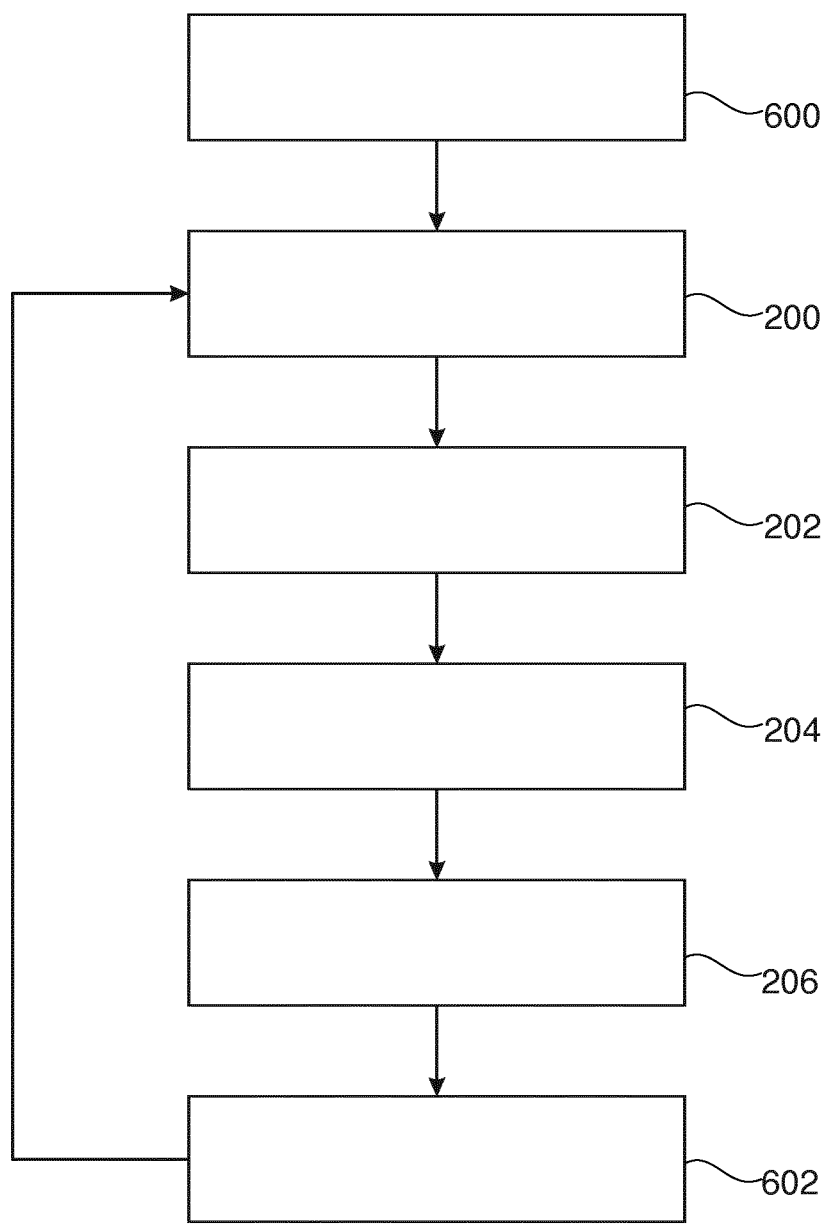
FIG. 6 shows a flow chart which illustrates a method of operating the medical instrument of FIG. 5.

FIG. 6 shows a flowchart which illustrates a method of operating the medical instrument 500 of FIG. 5. First in step 600 the radiotherapy instructions 560 are received. Next the method proceeds to step 200-206 as is illustrated in FIG. 2. After step 206 is performed the method proceeds to step 602 where the radiotherapy system is controlled to irradiate the target zone 538 using the radiotherapy instructions 560 and the combined motion signal 148. For example, the combined motion signal 148 could be used for gating the irradiation of the target zone 538 or it could also be used for adjusting the location of the target zone 538 as the subject 118 moves voluntarily or involuntarily.

High quality triggering in medical imaging (especially MR) is useful for a large number of examinations, e.g. cardiac-, abdominal- or pelvis-imaging. Trigger signals (combined motion signal) for the imaging sequence (pulse sequence commands) can be carried out at equal expiration states or equal points during the cardiac cycle resulting in superior image quality. Typically, vital signs are recorded using dedicated sensors, which are expensive as well as prone to errors and misplacements. Furthermore, bulk motion of the patient is often an issue, especially during MR imaging where scans can last up to several minutes and exams up to an hour.

Some examples do away with contact sensors such as a breathing belt or PPU-sensor for cardiac monitoring and replaces them with two contactless methods for vital sign detection. It has been demonstrated previously, that contactless methods are at least on par with conventional sensors but cheaper and more reliable. Furthermore, combining radar and optical detection techniques provides improved signal quality using cross correlations between systems, improved calibration schemes, or (spatial) guidance of one system using the other. E.g. radar can penetrate into the body and is better suited to sense motion of internal organs than the camera. The camera on the other hand is better suited to sense exceptional events like gross patient motion during which the radar signal is unreliable.

Examples may comprise an array of cheap (ultra-wideband) radar sensors in or below the patient bed of an imaging machine as well as an optical or infrared camera close to the bore observing the patient during imaging.

Both systems are connected to a computer that derives the breathing and/or cardiac signals from the raw data. For the optical part as well as the radar part suitable algorithms are available.

While both entities now can produce vital sign data (radar signal and movement signal), these signals can be combined for e.g. deriving a better signal to noise ratio or e.g. the radar array can provide a region of interest for the optical system, which can than zoom in order to produce best possible output instead of monitoring a larger area with relatively low signal.

Both Ultrawide band (UWB) radar as well as optical systems for vital sign detection have been presented by different groups showing the feasibility of such systems. For the optical part the system may comprise a camera with suitable optics located close to the bore and a software algorithm that computes breathing signals from feature movement in video stream or cardiac signals from skin color variation of the patient in the video.

The radar array system can conveniently be located in or below the patient bed allowing for large coverage of the patient's upper body. Systems operating on different frequencies in the GHz range have been demonstrated as well as ultra-wideband solutions. Breathing or cardiac signals can be computed from reflections in the body or from time-of-flight measurements.

For deriving and improved breathing trigger, the system may work as follows:

Example 1

Both systems provide a breathing curve and trigger points derived from the video and radar measurements.

The independent measurements are then correlated and an improved trigger is generated.

Example 2

Both systems provide a breathing curve and trigger points derived from the video and radar measurements.

In the spatially resolved radar data a region with best SNR is determined and the coordinates are handed over to the optical system.

The camera view is adjusted to this ROI (viewing angle, zoom, exposure . . . ) and a higher quality breathing curve can be generated.

Figure 7:
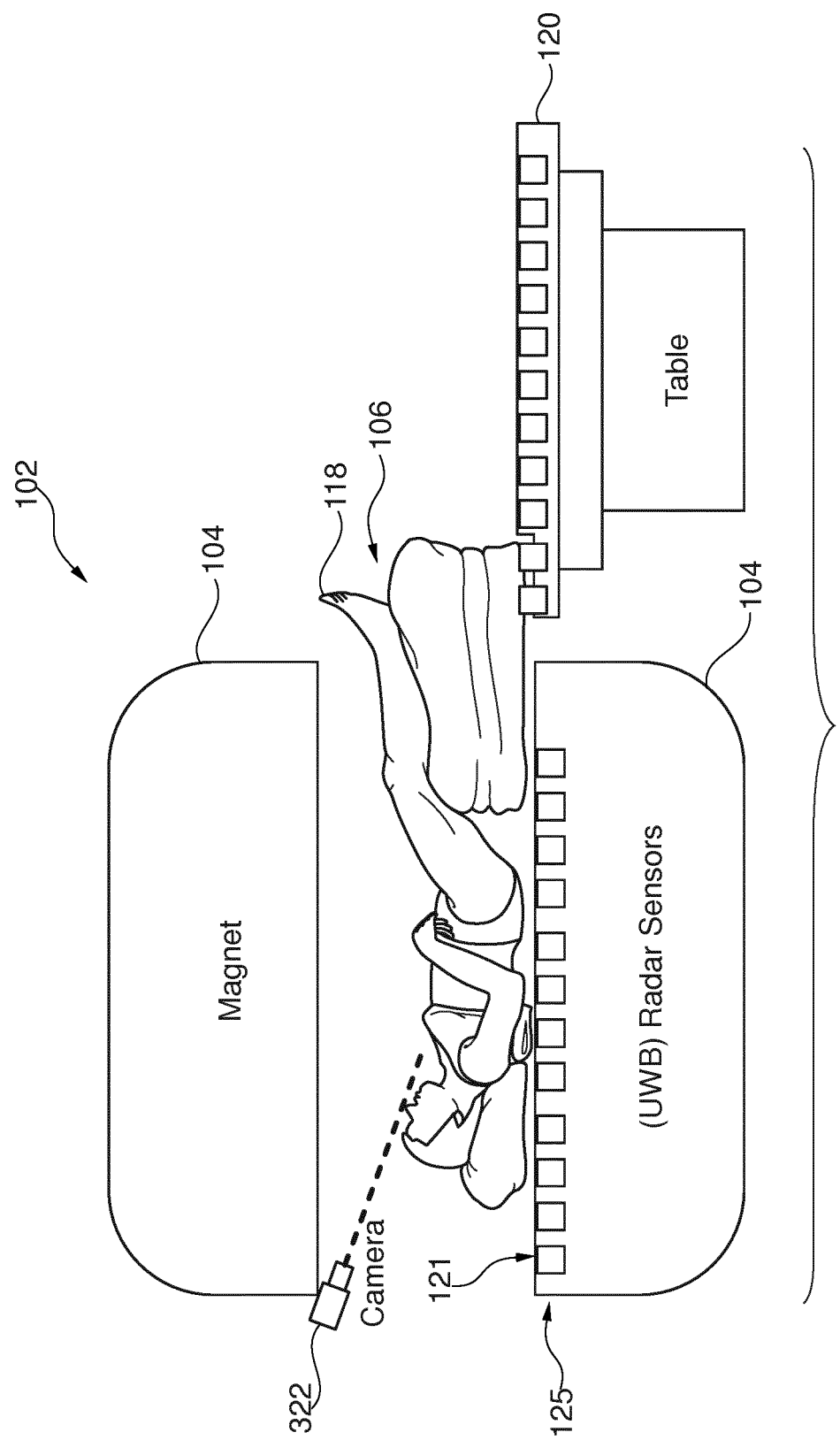
FIG. 7 illustrates a further example of a medical instrument.

FIG. 7 shows a further view of the medical imaging system 300. In the example shown in FIG. 7 the radar sensors 125 are located in or beneath the subject support 120 in an array-like fashion. Additionally, one or more cameras 322 may observe the patient or subject 118 in the bore 106 of the magnet 104.

Figure 8:
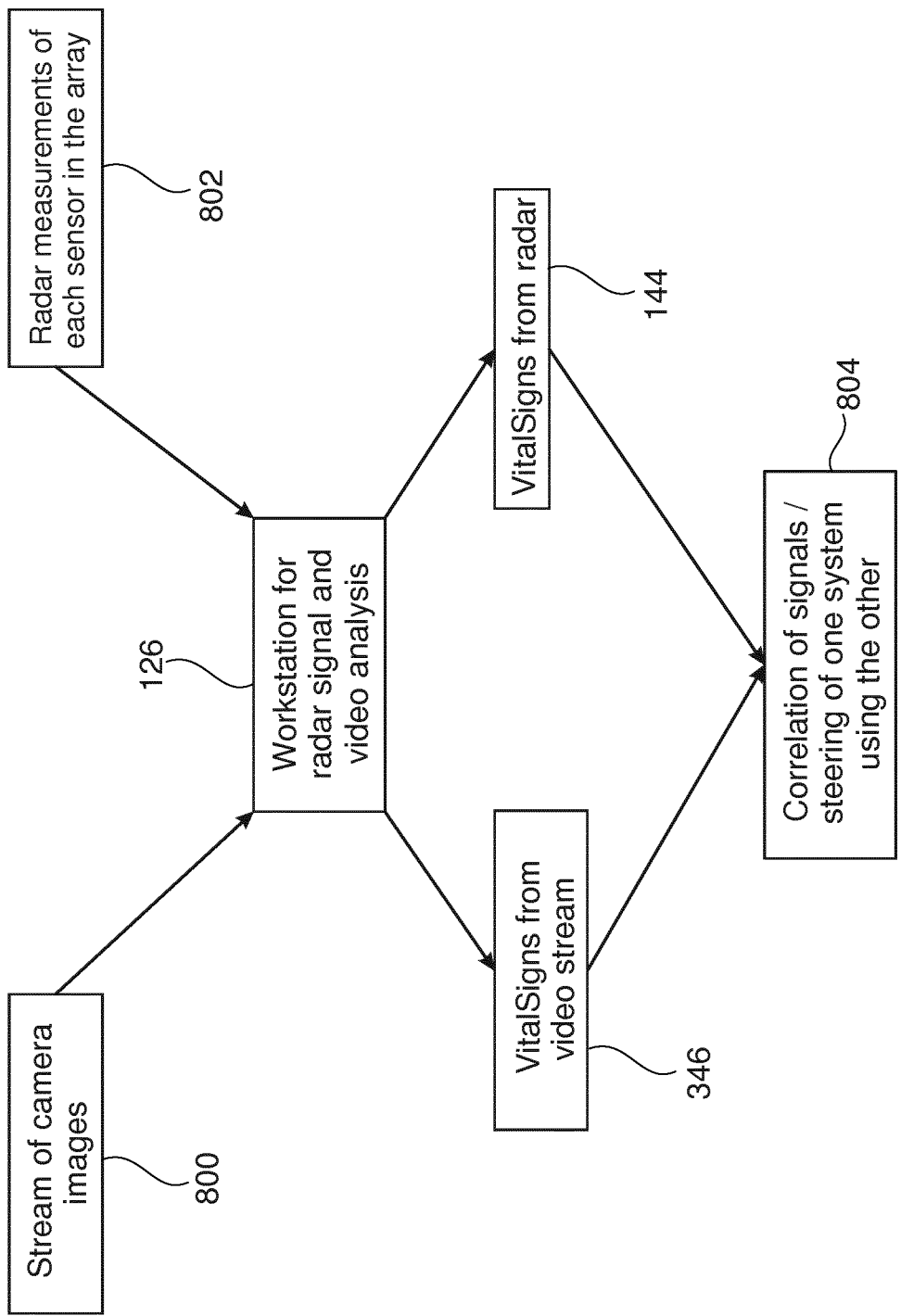
FIG. 8 shows a flow chart which illustrates a method of calculating a combined motion signal.

FIG. 8 shows a flowchart of a signal stream for calculating the combined motion signal. The motion shows a string of camera images 800 received from the camera 322 and a radar measurement 802 of each sensor 125 in the array. The signals are then processed, for example by computer 126 or a workstation for radar signals and video analysis. The result of this processing is the motion signal or image data 346 or a video stream. The radar data 144 is also produced. Block 804 shows that the signals 346 and 144 are correlated and combined. The output of block 804 is the combined motion signal 148. In FIG. 8, The input from both individual system are analyzed. Then either improved trigger signals are generated using e.g. correlation of the signals or the output of one system is used to set a region of interest for the other device thus improving the overall signal quality. The Workstation for radar signal- and video analysis can also be substituted by a local DSP processing unit in or close to the MR bore or integrated in the patient bed.

As an alternative to optical sensors such as cameras, ultrasound systems can also be used. Both (UWB) radar as well as Doppler ultrasound (DUS) (ultrasound imaging system) for vital sign detection have been presented by different groups showing the feasibility of such systems. Ultrasonic sensors generate acoustic signals and also detect returned signals. Doppler ultrasound (DUS) reflects the physiologic activity of the heart in terms of blood flow and cardiac wall motion and hence directly monitors the cardiac cycle in real time. Moreover, depending on the location of the transducer, the DUS signal corresponds to distinct times in the cardiac cycle, potentially providing more precise information for cardiac triggering than conventional ECG. Both methods can be used simultaneously and provide better vital signs recording and trigger signals.

Examples may comprise an array of inexpensive (ultra-wideband) radar sensors in or below the patient bed or integrated in the RF coil of an imaging machine as well as ultrasound detection system (DUS). Both systems are connected to a computer that derives the breathing and/or cardiac signals from the raw data. For the DUS as well as the radar part suitable algorithms are available.

While both entities can produce vital sign data, these signals can be combined for e.g. deriving a better signal to noise ratio or for steering purposes. So the radar array can provide a region of interest for the DUS system, which can than zoom in for detection of organ specific motion (heart, lung, liver) in order to produce best possible or improved output instead of monitoring a larger area with relatively low signal.

For the Ultrasound (US) part, the sensor consists of a local array of US sensors, which is integrated in a gel pad, providing contact with the skin of the patient and a software algorithm that computes breathing signals from feature movement in the video stream or cardiac signals from skin color variation of the patient in the video.

The radar array system can conveniently be located adjacent to the US sensor or in or below the patient bed or integrated in the RF coil, allowing for large coverage of the patient's upper body. Systems operating on different frequencies in the GHz range have been demonstrated as well as ultra-wideband solutions. Breathing, organ motion or cardiac signals can be computed from reflections in the body or from time-of-flight measurements.

For deriving and improved breathing trigger, the system may work as follows:

Example 1

Both systems provide a breathing curve and trigger points derived from the ultrasound and radar measurements.

The independent measurements are then correlated and an improved trigger is generated.

Example 2

Both systems provide a breathing curve and trigger points derived from the ultrasound and radar measurements.

In the spatially resolved radar data a region with best SNR is determined and the coordinates are handed over to the ultrasound system which then detects the VitalSigns locally with high SNR.

When located in an RF-coil, the data handling of the US sensor data as well as the power supply may be handled with the digital RXE-modules already present in the coil.

Figure 9:
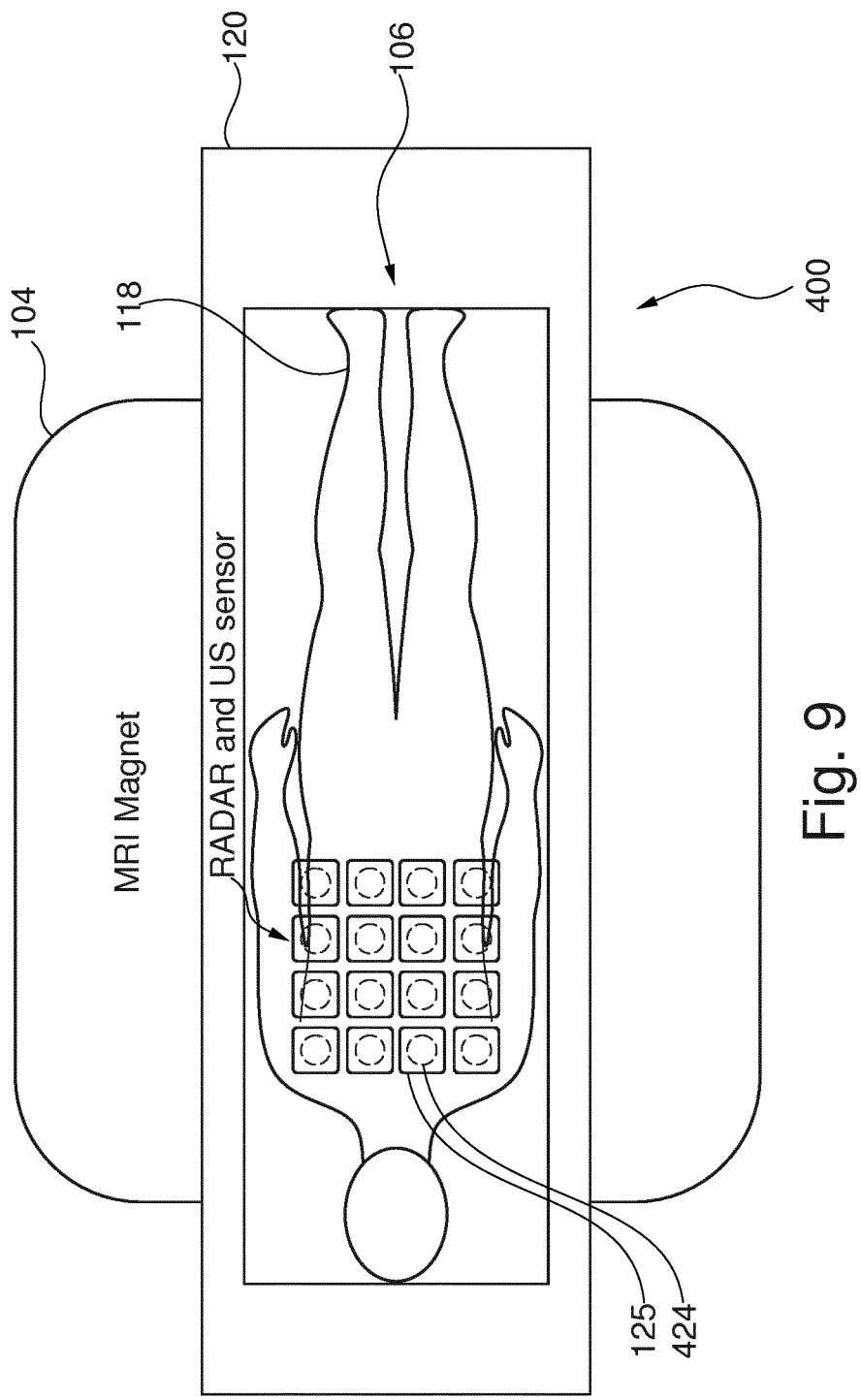
FIG. 9 illustrates a further example of a medical instrument.

FIG. 9 shows a further view of the medical instrument 400. A top view is shown with a subject 118 reposing on the subject support 120. There is an array of radar elements 125. In this example there is an ultrasonic transducer 424 located above and within each of the radar elements 125. The radar sensors and US sensors are located in or beneath the patient support in an array fashion or integrated in RF coil.

Figure 10:
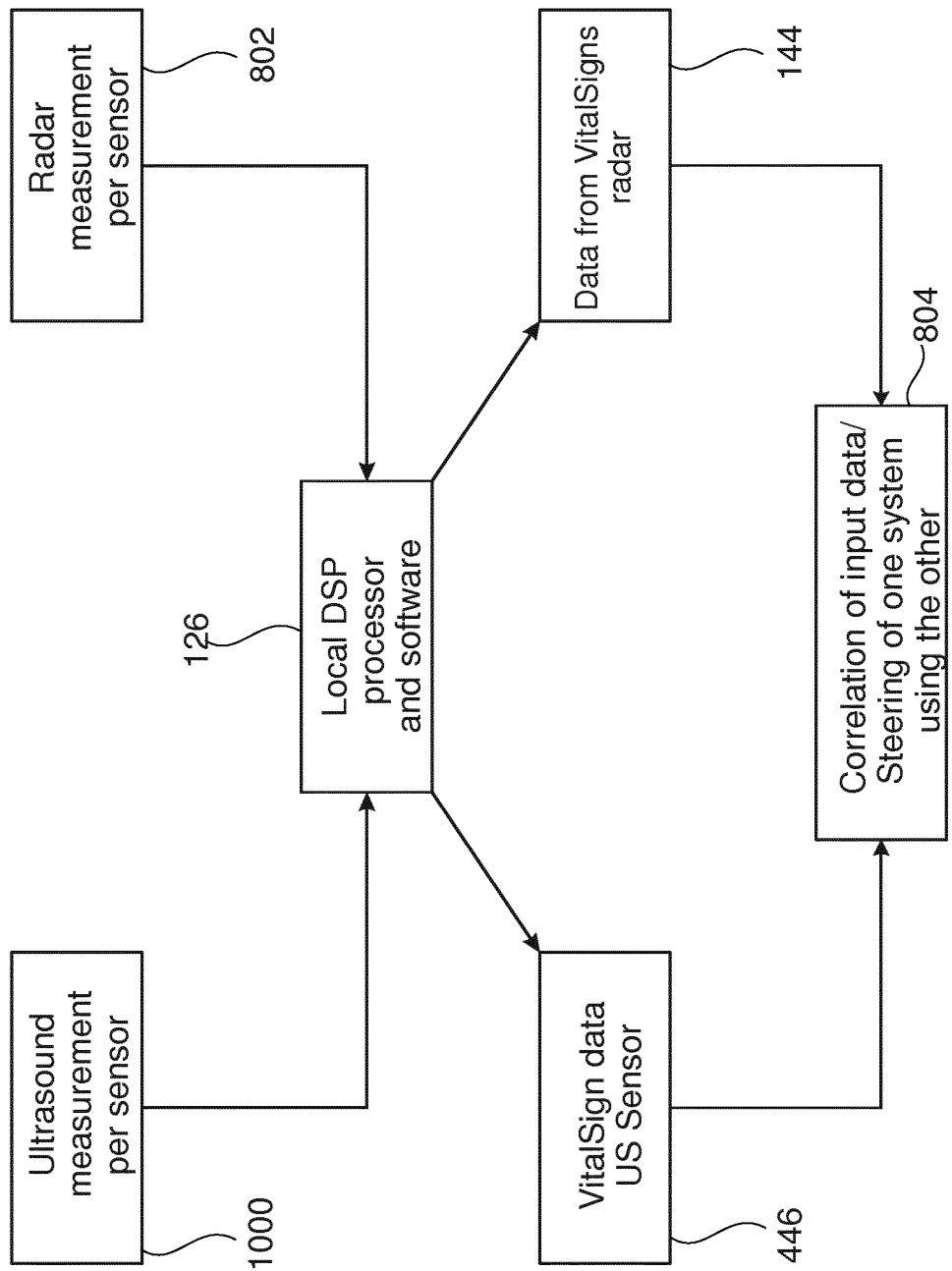
FIG. 10 shows a flow chart which illustrates a further method of calculating a combined motion signal.

FIG. 10 shows a flowchart which illustrates a signal flow in the process of making the combined motion signal 148. The input is the ultrasound data 1000 that is measured per ultrasonic transducer. Also, input is the radar measurement per radar element 125. These are then put into a local DSP processor or computer 126. The output of this is the ultrasound data 446 and the radar signal 144. These are then correlated in block 804. The output is the combined motion signal 148. The input from both individual system are analyzed. Then either improved trigger signals are generated using e.g. correlation of the signals or the output of one system is used to set a region of interest for the other device thus improving the overall signal quality. Workstation for radar signal and ultrasound analysis can also be substituted by local DSP processing unit in or close to the MR bore or integrated in the patient bed.

In some examples, the medical instrument further comprises a machine-learning module with deep learning capability adapted for receiving the sensed RADAR and optical motion signals. Deep learning methods aim at learning feature hierarchies with features on higher levels of the hierarchy formed by the composition of lower level features. They may include learning methods for a wide array of deep architectures, including neural networks with hidden layers and graphical models with levels of hidden variables.

Unsupervised pre-training renders learning deep architectures more effective. Such pre-training acts as a kind of network pre-conditioner, putting the parameter values in the appropriate range for further supervised training and initializes the model to a point in parameter space that renders the optimization process more effective, in the sense of achieving a lower minimum of the empirical cost function.

In one example, RADAR and Optical Signals are simultaneously acquired. This allows for real-time correlation and also correction of one signal using the other.

In one example, one of the radar system and the motion detection system (preferably the Radar-device) is coupled to an optical system such, that information is transmitted on where to focus spatially. The optical system can additionally generate information for checking if a coil is placed or not.

In one example, Moving bed signals are detected simultaneously by both sensors, filtered and correlated, but at certain areas only one of the signals may be sufficient.

In one example, one of the radar system and the motion detection system delivers motion detection while the other supplies a cardiac signal. Simultaneous detection and correlation allows to generate a motion vector field that can be used to denoise the cardiac trigger signal.

In another example, inner organ motion can be deduced from RADAR, surface motion (skin, cloth, coils, . . . ) is detected by an optical device such as a camera.

In some examples, the possible correlation mechanisms between the radar signal and the movement signal may include one or more of the following:

Cross-correlation of the radar and optical signal in order to check similarity of signals and find false positives/negatives)

Multiplication of generated trigger curves from both sources. Yields a curve with pronounced maxima and minima, when the signals coincide (time-wise). Can be used to measure a possible delay between the systems (depending on the area of the body each system is addressing.

Signal-nulling: subtract scaled versions of both signal and time shift, such that the remaining signal is essentially zero. This can also be used for delay measurement. Once the delay is known both signals may be added with determined time-shift for improved SNR.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical instrument
102 magnetic resonance imaging system
104 magnet
106 bore of magnet
108 imaging zone
109 region of interest
110 magnetic field gradient coils
112 magnetic field gradient coil power supply
114 radio-frequency coil
116 transceiver
118 subject
120 subject support
121 support surface
122 motion detection system
124 radar system
125 radar array
126 computer system
128 hardware interface
130 processor
132 user interface
134 computer memory
140 machine executable instructions
142 pulse sequence commands
144 radar signal
146 movement signal
148 combined motion signal
150 magnetic resonance imaging data
152 magnetic resonance image
154 machine learning algorithm
200 continuously receive the radar signal from the radar system
202 continuously receive the movement signal from the motion detection system
204 continuously calculate a combined motion signal from the radar system and the movement signal
206 control the magnetic resonance imaging system with the pulse sequence commands to acquire the magnetic resonance imaging data
300 medical instrument
322 camera
324 remotely controllable camera mount
346 image data
350 focus location
400 medical imaging system
422 ultrasound imaging system
424 ultrasound transducers
446 ultrasound data
500 medical instrument
502 radiotherpay system
506 gantry
508 radiotherapy source
510 collimator
514 cryostat
516 superconducting coil
518 superconducting shield coil
528 body coil
537 mechanical positioning system 538 target zone
540 axis of gantry rotation
542 radiation beam
560 radiotherapy instructions
600 receive radiotherapy instructions configured for controlling the radiotherapy system to irradiate a target zone of the subject
602 control the radiotherapy system to irradiate the target zone using the radiotherapy instructions and the combined motion signal
800 camera images
802 radar measurement
804 correlation and/or combination of signals
1000 ultrasound measurement

The invention claimed is:

1. An instrument, comprising:
a magnetic resonance imaging system, wherein the magnetic resonance imaging system is configured to acquire magnetic resonance imaging data from an imaging zone;
a subject support, wherein the subject support is configured to support at least a portion of a subject within the imaging zone, wherein the subject support comprises a support surface, wherein the support surface is configured to receive the subject, wherein the subject support comprises a plurality of radar sensors embedded below the support surface, wherein the plurality of radar sensors are configured as a radar array;
a radar system, wherein the radar system is configured to acquire a radar signal from the subject via the plurality of radar sensors of the radar array;
a motion detection system, wherein the motion detection system comprises at least one motion detection system sensor, wherein the at least one motion detection system sensor is distinct from the radar sensors, wherein the motion detection system is configured to acquire a movement signal via the at least one motion detection system sensor, wherein the movement signal is produced in response to movement by the subject, wherein the motion detection system is separate and distinct from the radar system, and wherein the movement signal is distinct from the radar signal;
a memory, wherein the memory is arranged to store machine executable instructions and pulse sequence commands;
a processor circuit, wherein the processor circuit is arranged to control the medical instrument,
wherein execution of the machine executable instructions causes the processor circuit to:
continuously receive the radar signal from the radar system;
continuously receive the movement signal from the motion detection system;
continuously calculate a combined motion signal from the radar signal and the movement signal; and
control the magnetic resonance imaging system with the pulse sequence commands to acquire the magnetic resonance imaging data, wherein the acquisition of the magnetic resonance imaging data is controlled using the combined motion signal.

2. The instrument of claim 1, wherein the combined motion signal comprises at least one of the following: a cardiac phase motion signal, a breathing phase motion signal, and a voluntary motion signal.

3. The instrument of claim 2, wherein acquisition of the radar signal and acquisition of the movement signal are independent of each other, and wherein the combined motion signal is calculated by cross correlating the radar signal with the movement signal to identify similar signals and reject false signals.

4. The instrument of claim 1, wherein the combined motion signal is continuously calculated using a machine learning algorithm.

5. The medical instrument of claim 4, wherein execution of the machine executable instructions further causes the processor circuit to:
receive a preliminary radar signal from the radar system;
receive a preliminary movement signal from the motion detection system, wherein the preliminary movement signal is acquired simultaneously with the preliminary radar signal;
receive a heart rate signal from a heart rate monitor, wherein the heart rate signal is acquired simultaneously with the preliminary radar signal;
receive a breathing signal from a breathing monitor, wherein the breathing signal is acquired simultaneously with the preliminary radar signal; and
train the machine learning algorithm using the preliminary radar signal, the preliminary movement signal, the heart rate signal, and the breathing signal.

6. The instrument of claim 4, wherein the machine learning algorithm is an unsupervised statistical learning algorithm, and wherein execution of the machine executable instructions further causes the processor circuit to train the machine learning algorithm on the fly as the radar signal and the movement signal are received.

7. The instrument of claim 2, wherein one of the movement signal and the radar signal supplies a cardiac motion signal, and the other of the movement signal and the radar signal supplies a body motion signal, wherein execution of the machine executable instructions further cause the processor to calculate a motion vector field using the cardiac motion signal and the body motion signal, and wherein the cardiac motion signal is denoised using the motion vector field.

8. The instrument of claim 1, wherein the motion signal comprises chest motion, and wherein the at least one motion detection system sensor comprises a camera, wherein the camera is configured for capturing images of the chest motion.

9. The instrument of claim 8, wherein the magnetic resonance imaging system further comprises a remotely controllable camera mount configured for remotely pointing the camera, wherein execution of the machine executable instructions further causes the processor circuit to:
determine a focus location using the radar signal; and
control the remotely controllable camera mount to point the camera at the focus location.

10. The instrument of claim 1, wherein the motion detection system comprises an ultrasound imaging system, and wherein the at least one motion detection system sensor comprises a plurality of ultrasound transducers configured in an ultrasound transducer array, wherein the ultrasound imaging system comprises the plurality of ultrasound transducers, and wherein the movement signal is produced by the ultrasound imaging system via the plurality of ultrasound transducers.

11. The instrument of claim 10, wherein the ultrasound transducers are distributed across the support surface, or wherein the ultrasound imaging system is a High Intensity Focused Ultrasound (HIFU) system mounted in the subject support.

12. The instrument of claim 10, wherein the ultrasound imaging system has an adjustable field of view, wherein execution of the machine executable instructions further causes the processor circuit to:
  determine a focus location using the radar signal; and
  control the adjustable field of view so that the focus location is within the adjustable field of view.

13. The instrument of claim 1, further comprising a radiotherapy system, wherein execution of the machine executable instructions further causes the processor circuit to:
  receive radiotherapy instructions configured for controlling the radiotherapy system to irradiate a target zone of the subject: and
  control the radiotherapy system to irradiate the target zone using the radiotherapy instructions and the combined motion signal, wherein the combined motion signal is used to modify the radiotherapy instructions and/or gate irradiation by the radiotherapy system.

14. The instrument of claim 1,
  wherein the motion detection system has an adjustable field of view,
  wherein execution of the machine executable instructions further causes the processor circuit to:
    determine a focus location using the radar signal; and
    control the adjustable field of view of the motion detection system so that the focus location is within the adjustable field of view.

15. The instrument of claim 1, wherein acquisition of the radar signal and acquisition of the movement signal are independent of each other, and wherein the combined motion signal is calculated by at least one of the following:
  multiplying the radar signal with the movement signal to determine when the radar signal and movement signal coincide; and
  adding the radar signal with the movement signal using a corrective phase shift.

16. A tangible computer program product comprising machine executable instructions stored on a non-transitory computer readable medium, wherein the machine executable instructions when executed by a processor circuit cause the processor circuit to control an instrument, wherein the instrument comprises a magnetic resonance imaging system, wherein the magnetic resonance imaging system is configured to acquire magnetic resonance imaging data from an imaging zone, wherein the instrument comprises a subject support, wherein the subject support is configured to support at least a portion of a subject within the imaging zone, wherein the subject support comprises a support surface, wherein the support surface is configured to receive the subject, wherein the subject support comprises a plurality of radar sensors embedded below the support surface, wherein the plurality of radar sensors are configured as a radar array, wherein the instrument further comprises a radar system, wherein the radar system is configured to acquire a radar signal from the subject via the plurality of radar sensors of the radar array, wherein the medical instrument further comprises a motion detection system, wherein the motion detection system comprises at least one motion detection system sensor, wherein the at least one motion detection system sensor is distinct from the radar sensors, wherein the motion detection system is separate and distinct from the radar system, wherein the motion detection system is configured to acquire a movement signal, wherein the movement signal is produced in response to movement by the subject, and wherein the movement signal is distinct from the radar signal,
  wherein execution of the machine executable instructions causes the processor circuit to:
    continuously receive the radar signal from the radar system;
    continuously receive the movement signal from the motion detection system;
    continuously calculate a combined motion signal from the radar signal and the movement signal; and
    control the magnetic resonance imaging system with pulse sequence commands to acquire the magnetic resonance imaging data, wherein the acquisition of the magnetic resonance imaging data is controlled using the combined motion signal.

17. A method of operating an instrument, wherein the instrument comprises a magnetic resonance imaging system, wherein the magnetic resonance imaging system is configured to acquire magnetic resonance imaging data from an imaging zone, wherein the instrument comprises a subject support, wherein the subject support is configured to support at least a portion of a subject within the imaging zone, wherein the subject support comprises a support surface, wherein the support surface is configured to receive the subject, wherein the subject support comprises a plurality of radar sensors embedded below the support surface, wherein the plurality of radar sensors are configured as a radar array, wherein the medical instrument further comprises a radar system, wherein the radar system comprises the radar array, wherein the medical instrument further comprises a motion detection system, wherein the motion detection system comprises at least one motion detection system sensor, wherein the at least one motion detection system sensor is distinct from the radar sensors, and wherein the motion detection system is separate and distinct from the radar system, the method comprising:
  the radar system acquiring a radar signal from the subject from the plurality of radar sensors of the radar array;
  the motion detection system acquiring a movement signal via the at least one motion detection system sensor, wherein the movement signal is produced in response to movement by the subject, and wherein the movement signal is distinct from the radar signal;
  a processor circuit continuously receiving the radar signal from the radar system;
  the processor circuit continuously receiving the movement signal from the motion detection system;
  the processor circuit continuously calculating a combined motion signal from the radar signal and the movement signal; and
  the processor circuit controlling the magnetic resonance imaging system with pulse sequence commands to acquire the magnetic resonance imaging data, wherein the acquisition of the magnetic resonance imaging data is controlled using the combined motion signal.

18. The method of claim 17, further comprising:
  receiving a preliminary radar signal from the radar system;
  receiving a preliminary movement signal from the motion detection system, wherein the preliminary movement signal is acquired simultaneously with the preliminary radar signal;
  receiving a heart rate signal from a heart rate monitor, wherein the heart rate signal is acquired simultaneously with the preliminary radar signal;
  receiving a breathing signal from a breathing monitor, wherein the breathing signal is acquired simultaneously with the preliminary radar signal; and
  training a machine learning algorithm using the preliminary radar signal, the preliminary movement signal, the heart rate signal, and the breathing signal, wherein the machine learning algorithm continuously calculates the combined motion signal.

19. The method of claim 18, wherein the machine learning algorithm is an unsupervised statistical learning algorithm, the method comprising training the machine learning algorithm on the fly as the radar signal and the movement signal are received.

20. The method of claim 17,
wherein the radar signal supplies a cardiac motion signal,
wherein the movement signal supplies a body motion signal,
wherein the method further comprises:
  calculating a motion vector field using the cardiac motion signal and the body motion signal, and
  denoising the cardiac motion signal using the motion vector field.

* * * * *